US012558105B2

(12) United States Patent
Fang et al.

(10) Patent No.: US 12,558,105 B2
(45) Date of Patent: Feb. 24, 2026

(54) DETACHABLE RONGEUR

(71) Applicant: Aesculap AG, Tuttlingen (DE)

(72) Inventors: Zhihao Fang, Suzhou (CN); Jiasheng Huang, Suzhou (CN)

(73) Assignee: Aesculap AG, Tuttlingen (DE)

( * ) Notice: Subject to any disclaimer, the term of this patent is extended or adjusted under 35 U.S.C. 154(b) by 169 days.

(21) Appl. No.: 18/402,152

(22) Filed: Jan. 2, 2024

(65) Prior Publication Data

US 2024/0130738 A1     Apr. 25, 2024
US 2024/0225664 A9     Jul. 11, 2024

Related U.S. Application Data

(63) Continuation of application No. PCT/EP2022/068473, filed on Jul. 4, 2022.

(30) Foreign Application Priority Data

Jul. 2, 2021   (CN) .......................... 202110748796.9
Jul. 2, 2021   (CN) .......................... 202121496060.9

(51) Int. Cl.
*A61B 17/16*          (2006.01)
(52) U.S. Cl.
CPC ................................. *A61B 17/1611* (2013.01)
(58) Field of Classification Search
CPC ............ A61B 17/1604; A61B 17/1606; A61B 17/1608; A61B 17/1611
See application file for complete search history.

(56) References Cited

U.S. PATENT DOCUMENTS

| | | | |
|---|---|---|---|
| 6,517,545 B1 * | 2/2003 | Mazur ................ | A61B 17/1606 606/174 |
| 6,699,254 B1 * | 3/2004 | Tontarra ............. | A61B 17/1611 606/83 |
| 2013/0041379 A1 * | 2/2013 | Bodor ................ | A61B 17/1611 606/83 |

FOREIGN PATENT DOCUMENTS

| | | | | |
|---|---|---|---|---|
| CN | 111728666 A | * | 10/2020 | ......... A61B 17/1606 |
| DE | 10022908 A1 | | 11/2001 | |
| EP | 1092397 A1 | | 4/2001 | |

OTHER PUBLICATIONS

Search Report received in International Application No. PCT/EP2022/068473 dated Oct. 7, 2022, 3 pages.
Written Opinion received in International Application No. PCT/EP2022/068473 dated Oct. 7, 2022, 7 pages.

* cited by examiner

*Primary Examiner* — Si Ming Ku
(74) *Attorney, Agent, or Firm* — Christoper A. Rothe; CM Law

(57)          ABSTRACT

A detachable rongeur has a main body, a slider and a movable handle. A front end of the main body has a cutting edge. The movable handle is hinged to both the main body and the slider. The movable handle can drive the slider to move along first sliding grooves. A cheek portion of the main body includes a trigger lock catch structure. The movable handle can be pulled back and forth. An upper portion of the movable handle includes a first feature portion and a second feature portion that are sequentially arranged from bottom to top. The trigger lock catch structure abuts against the first feature portion or the second feature portion.

19 Claims, 3 Drawing Sheets

DETACHABLE RONGEUR

CROSS-REFERENCE TO RELATED APPLICATIONS

This application is a continuation of International Application No. PCT/EP2022/068473, filed on Jul. 4, 2022, which claims priority to Chinese Application No. 202121496060.9, filed on Jul. 2, 2021, and which claims priority to Chinese Application No. 202110748796.9, filed on Jul. 2, 2021. The contents of International Application No. PCT/EP2022/068473, Chinese Application No. 202121496060.9 and Chinese Application No. 202110748796.9 are incorporated by reference herein in their entireties.

FIELD

The present disclosure relates to the technical field of medical instruments, and in particular to a detachable rongeur.

BACKGROUND

In clinical operations, especially in neurosurgical procedures, a rongeur surgical instrument, in particular a laminectomy rongeur surgical instrument, is usually needed to cut small bones and soft tissue. However, the existing rongeurs still have certain problems. Most of the traditional rongeurs cannot be disassembled but can only be cleaned as a whole, so that it is difficult to thoroughly clean bone residues, blood, tissue, etc. remaining in gaps, which is liable to cause serious consequences, such as cross infection, after long-term use.

At present, the detachable rongeurs available on the market can only be disassembled into parts for cleaning, which requires more assembly and disassembly time and is not conducive to rapid turnover of instruments, and also has placement position requirements. When many surgical instruments are cleaned and sterilized, it will take a lot of time to find paired slider and main body, and there is also a risk of loss.

In all the existing rongeurs, a spring piece is fixed to the rongeur in a screwed manner, so that it is difficult to clean the fixing area, and the spring is composed of a left piece and a right piece which are hinged or cross-connected in a screwed manner so that it is difficult to clean all the connections.

Therefore, it is necessary to provide a more applicable detachable rongeur, in particular a detachable laminectomy rongeur, to solve the above problems.

SUMMARY

The objective of the present disclosure is to provide a detachable rongeur, in particular a detachable laminectomy rongeur, which has the advantages of being, in particular, detachable, easy to clean, rapid assembly and disassembly, etc., and solves the problem of difficult and time-consuming cleaning of a rongeur and a paired structure being easy-to-lose.

In order to achieve the above objective, the present disclosure uses the following technical solution.

The present disclosure provides a detachable rongeur, in particular a detachable laminectomy rongeur, comprising a main body, a slider and a movable handle, wherein an upper portion of the main body is provided with first sliding grooves, the slider is located on the upper portion of the main body, an end surface of the side of the slider facing the main body is provided with first bosses which are embedded in the first sliding grooves, a front end of the main body is provided with a cutting edge; the movable handle is hinged to both the main body and the slider, and the movable handle can drive the slider to move along the first sliding grooves; a cheek portion of the main body is provided with a trigger lock catch structure; and the movable handle can be pulled back and forth, an upper portion of the movable handle is provided with a first feature portion and a second feature portion which are sequentially arranged from bottom to top, and the trigger lock catch structure abuts against the first feature portion or the second feature portion;

when the trigger lock catch structure abuts against the first feature portion, the movable handle is capable of driving the slider to move back and forth along the first sliding grooves, and in this case, the rongeur is in a working state; and when the movable handle is pulled forwards, the trigger lock catch structure abuts against the second feature portion, the slider is disengaged from the first sliding grooves, the slider forms a fixed angle with the main body under the limiting action of the trigger lock catch structure, and in this case, the rongeur is in a disassembled state.

Preferably, a rear end surface of the upper portion of the movable handle protrudes to form an arc boss, and a lower surface of the arc boss is in arc transition connection with a rear end surface of the movable handle to form the first feature portion; an upper surface of the arc boss is in arc transition connection with the rear end surface of the movable handle to form the second feature portion; and a first sliding portion is capable of moving on and abutting against the first feature portion or the second feature portion.

Preferably, the trigger lock catch structure is provided with a first sliding portion, a second sliding portion and a trigger portion, which are sequentially arranged from left to right; and when the rongeur is in the working state, the first sliding portion abuts against the first feature portion of the movable handle; and when the rongeur is in the disassembled state, the first sliding portion abuts against the second feature portion of the movable handle, and the trigger portion is connected to a rear end of the slider such that the slider forms a fixed angle with the main body.

Preferably, the trigger lock catch structure comprises a trigger member, a trigger screw, and a torsion spring sleeved on the trigger screw, wherein the cheek portion of the main body is provided with a hollow region in which the torsion spring is arranged, and the trigger screw penetrates from one side of the cheek portion of the main body to the opposite side of the cheek portion of the main body.

Preferably, the trigger member comprises the trigger portion, wherein the trigger portion is a key-shaped member, with an upper surface of the trigger portion being a flat surface; the end of the trigger portion close to the movable handle extends towards the movable handle to form a third boss; and an end surface of the third boss in contact with the movable handle forms the first sliding portion, and an arc-shaped surface, facing an interior of the third boss, provided at a lower portion of the third boss forms the second sliding portion, the first sliding portion abutting with and coming into contact with the first feature portion or the second feature portion, and the second sliding portion abutting with the torsion spring.

Preferably, the hollow region of the cheek portion of the main body is further provided with a limiting pin, wherein the limiting pin is arranged below the first sliding portion, the limiting pin has an axis parallel to that of the trigger screw, and one end of the torsion spring abuts against the limiting pin, and the other end of the torsion spring abuts against the second sliding portion; and when the rongeur is in the working state, the limiting pin abuts with a lower portion of the first sliding portion such that the first sliding portion abuts against the first feature portion.

Preferably, the main body is provided with a central screw, the movable handle is hinged to the main body by means of the central screw, and the movable handle is rotatable around the central screw.

Preferably, the end of the movable handle connected to the slider is provided with a kidney-shaped hole, and the slider is connected to the movable handle by means of a slider screw in cooperation with the kidney-shaped hole; when the rongeur is in the working state, the slider screw is located in the middle of the kidney-shaped hole; and when the rongeur is in the disassembled state, the slider screw is located in an upper portion of the kidney-shaped hole.

Preferably, a leaf spring, in particular V-shaped, is provided between the movable handle and the main body, wherein one end of the leaf spring is connected to the movable handle, the other end of the leaf spring is connected to the main body, and the leaf spring is of an integrally formed structure.

Preferably, the movable handle and the main body are oppositely provided with a clamping portion, end portions of two ends of the leaf spring are respectively provided with a fastener portion, and the fastener portions are detachably and fixedly connected to the clamping portion as a whole.

Preferably, the clamping portion comprises two clamping pieces parallel to each other, wherein a clamping groove is formed between the two clamping pieces, the two clamping pieces are correspondingly provided with through holes, outer edges of the through holes and the clamping pieces are provided with notches, and the clamping portion is clamped in the through holes from the notches.

Preferably, each fastener portion comprises symmetrical extending portions formed by an end portion of the leaf spring extending towards the outside of the leaf spring, the two extending portions forming a T-shaped structure with the end portion of the leaf spring, and the extending portions being clamped in the through holes.

Preferably, a front portion and a rear portion of the upper portion of the main body are respectively provided with first sliding grooves, a front portion and a rear portion of the slider are respectively and correspondingly provided with first bosses, an end surface of the slider, facing the main body, between the two first bosses is provided with a second sliding groove, and the main body between the two first sliding grooves is correspondingly provided with a second boss which is embedded in the second sliding groove.

Preferably, the main body and a holding portion of the movable handle are respectively provided with anti-slip lines.

Preferably, the end of the slider close to the trigger lock catch structure is configured to be a smooth curved surface, with the curvature of the curved surface being of a minimum value at the highest point of the curved surface.

The detachable rongeur of the present disclosure has the beneficial effects as follows.

Compared with the prior art, the rongeur has a disassembly function. After a surgical operation is completed, the handle is rotated, a trigger is gently pressed down, the handle is loosened, the slider automatically slides backwards to a final position, and then the slider may be rotated upwards such that the slider is opened and forms an angle with the main body for thoroughly cleaning and disinfecting a gap between the main body and the slider. In addition, the leaf spring is integrally formed and is connected to the main body and the handle by means of fasteners without a screw, thereby avoiding bone residues and soft tissue residues and reducing the occurrence of cross infection. After cleaning is completed, the slider is closed along a guide groove on the main body, and then the handle is closed, such that the trigger may automatically return by means of the torsion spring to enter the normal working state. The rongeur is simple to operate and is highly practicable.

Figure 1:
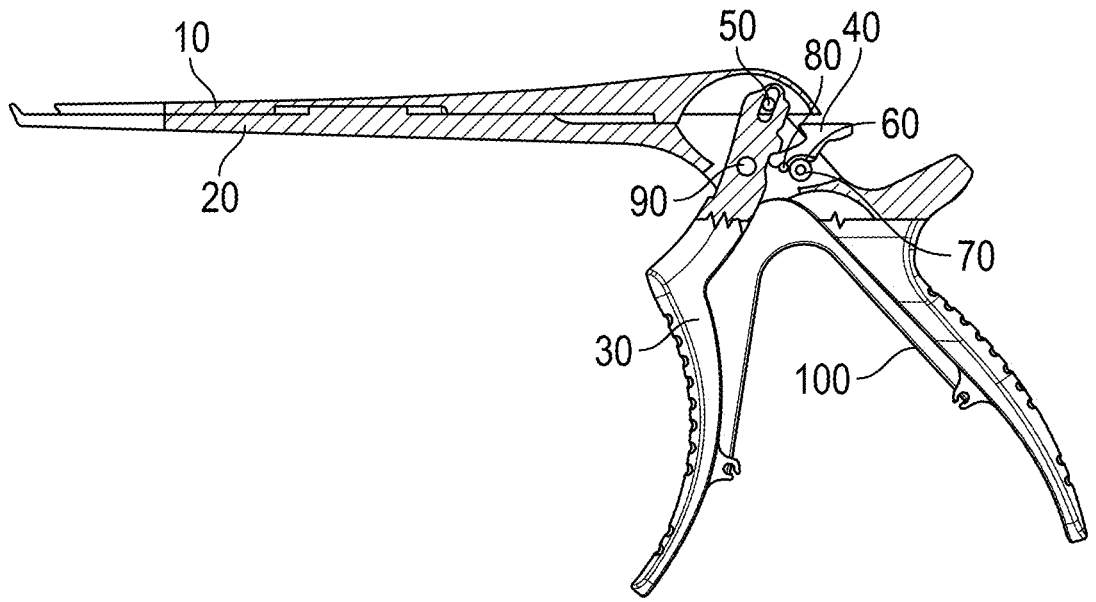
FIG. 1 is a first schematic diagram of a detachable laminectomy rongeur in a normal working state.
Figure 2:
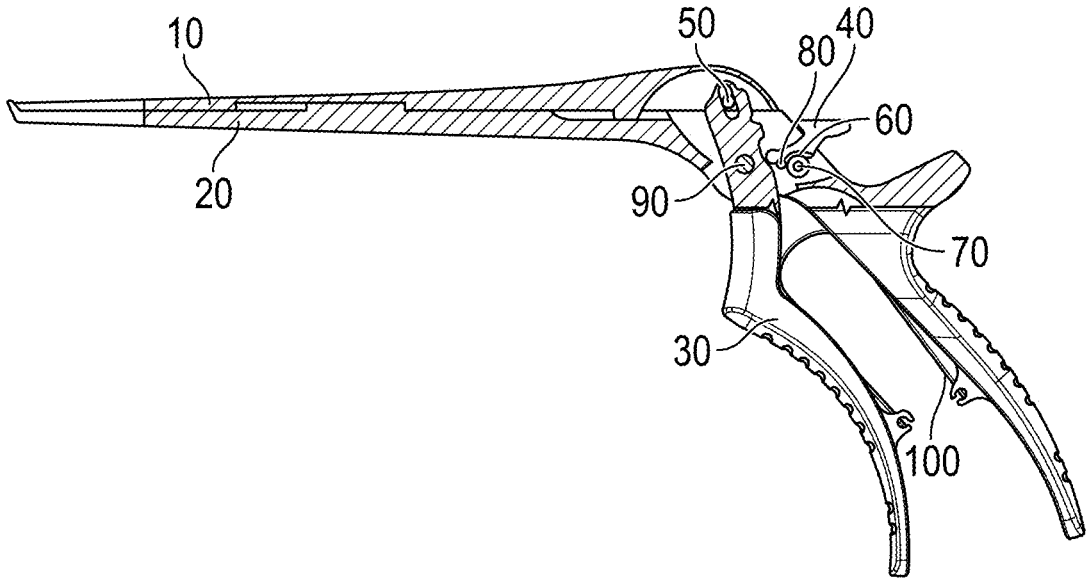
FIG. 2 is a second schematic diagram of the detachable laminectomy rongeur in the normal working state.
Figure 3:
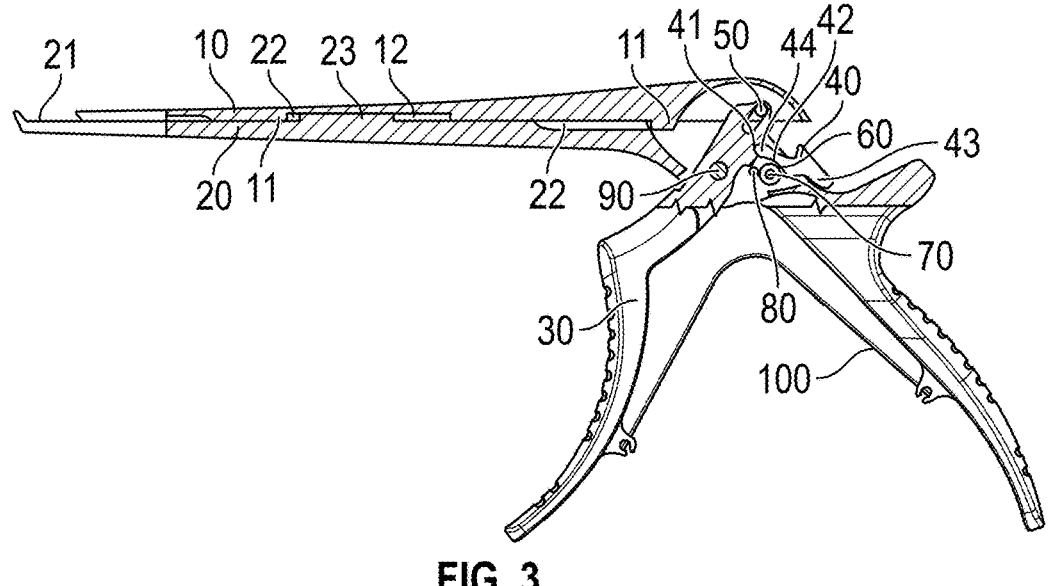
FIG. 3 is a first schematic diagram of the detachable laminectomy rongeur in a disassembled state.
Figure 4:
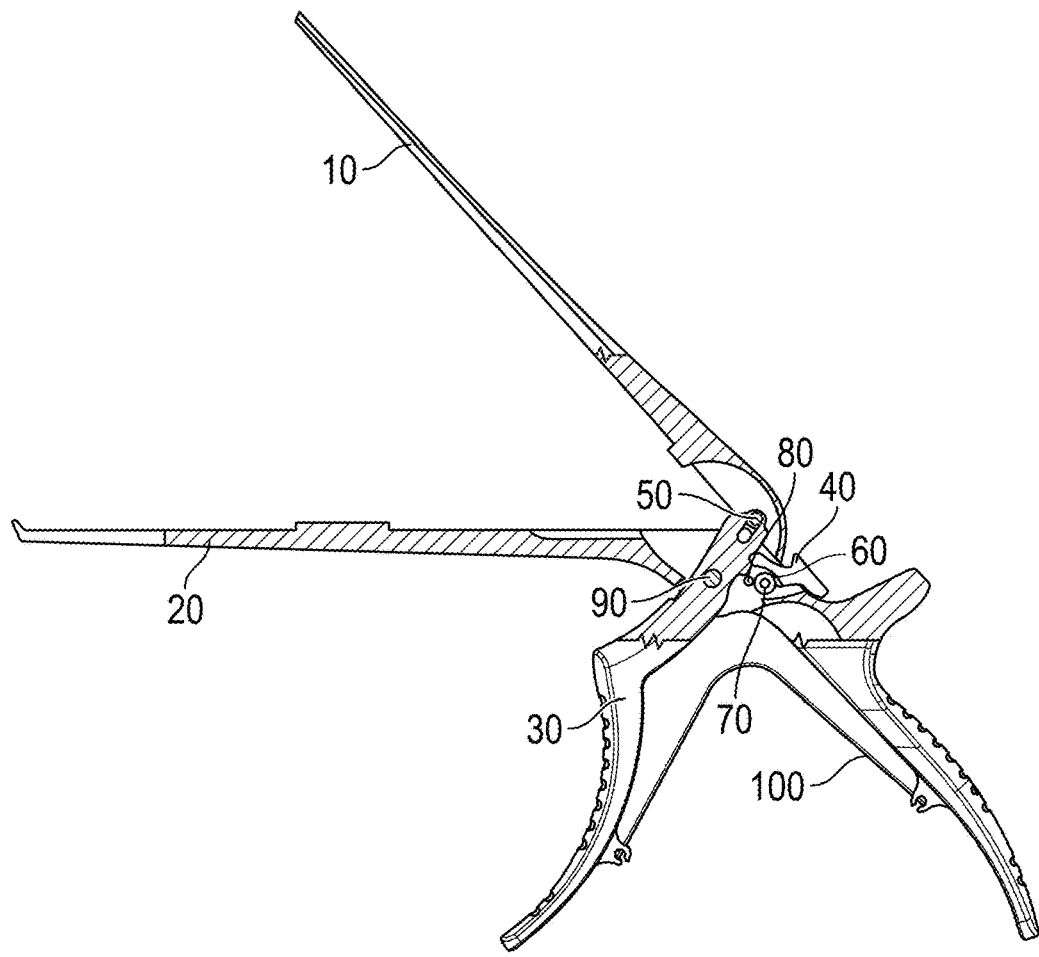
FIG. 4 is a second schematic diagram of the detachable laminectomy rongeur in the disassembled state.
Figure 5:
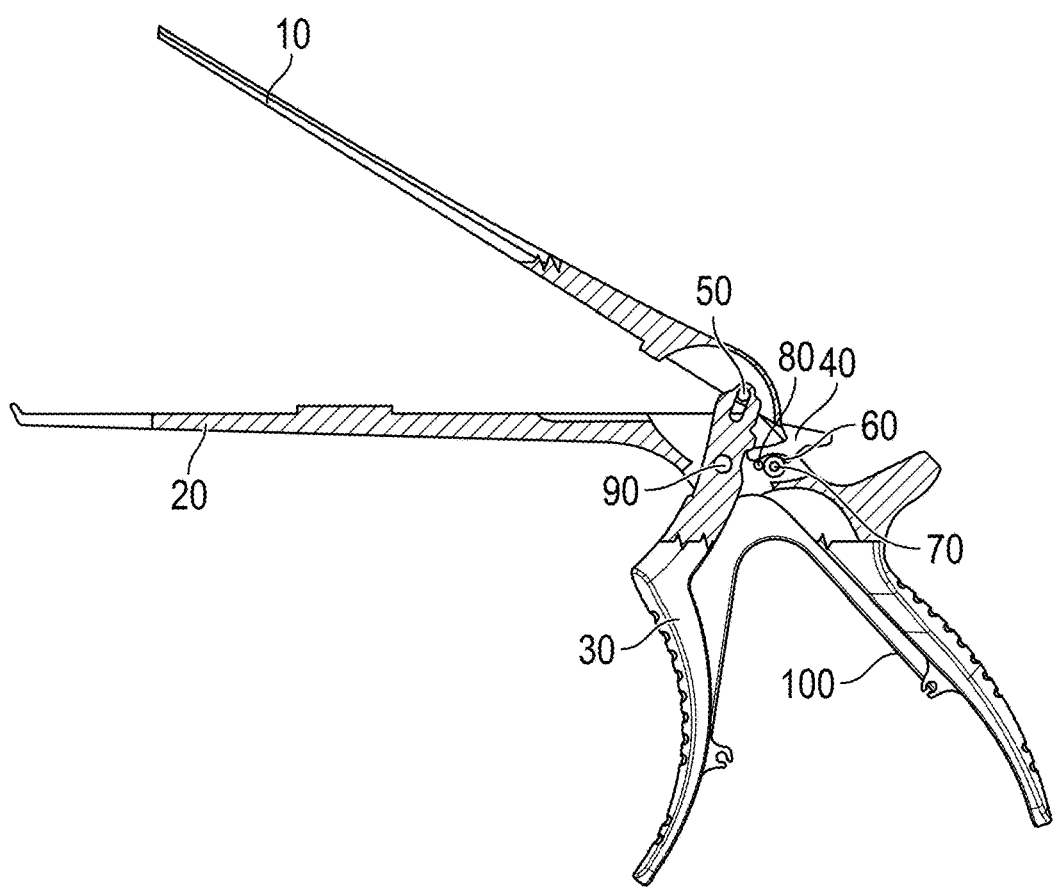
FIG. 5 is a third schematic diagram of the detachable laminectomy rongeur in the disassembled state.

In the figures: 10—slider, 11—first boss, 12—second sliding groove, 20—main body, 21—cutting edge, 22—first sliding groove, 23—second boss, 30—movable handle, 31—arc boss, 311—first feature portion, 312—second feature portion, 32—kidney-shaped hole, 40—trigger portion, 41—first sliding portion, 42—second sliding portion, 43—trigger member, 44—third boss, 50—slider screw, 60—torsion spring, 70—trigger screw, 80—limiting pin, 90—central screw, and 100—leaf spring.

DETAILED DESCRIPTION

The present disclosure will be further described below in conjunction with particular embodiments. The drawings are used for illustrative purposes only, are merely schematic diagrams rather than physical drawings, and may not be construed as limiting the present disclosure. In order to better illustrate the embodiments of the present disclosure, some components may be omitted, scaled up or scaled down in the drawings, which will not represent the actual size of products. It should be understood by those skilled in the art that some well-known structures and the illustration thereof in the drawings may be omitted.

The same or similar reference numerals in the drawings of the embodiments of the present disclosure correspond to the same or similar components. In the description of the present disclosure, it should be understood that the orientation or positional relationship indicated by the terms "upper", "lower", "vertical", "horizontal", "transverse", "longitudinal", etc. are based on the orientation or positional relationship shown in the drawings, which is only intended to facilitate the description of the present disclosure and simplifying the description, rather than indicating or implying that the device or element referred to must have a particular orientation or be constructed and operated in a particular orientation. Therefore, the terms intended to describe the positional relationship in the drawings are for illustrative purposes only and should not be construed as limiting the present disclosure.

In addition, some of the terms mentioned above may be used to represent other meanings in addition to the orientation or positional relationship. For example, the term "upper" may also be used to represent a certain attachment or connection relationship under some circumstances. For those of ordinary skill in the art, the specific meaning of the terms mentioned above in the present disclosure may be construed according to specific circumstances.

In addition, the terms "first", "second", etc. are used for descriptive purposes only, are mainly used for distinguishing different devices, elements or components (the specific types and structures may be the same or different), are not used for indicating or implying the relative importance and quantity of the indicated devices, elements or components, and should not be construed as indicating or implying the relative importance.

Figure 6:
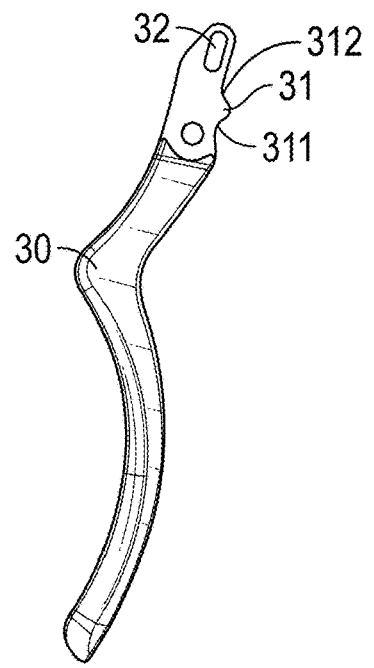
FIG. 6 is a structural schematic diagram of a slider, a main body and a trigger structure of the detachable laminectomy rongeur.

FIGS. 1-6 show an embodiment of a detachable laminectomy rongeur of the present disclosure. The detachable laminectomy rongeur provided in the present disclosure comprises a main body 20, a slider 10 and a movable handle 30. The main body 20 and a holding portion of the movable handle 30 are respectively provided with anti-slip lines, which increases the friction with a contact surface and are convenient for a user to hold. An upper portion of the main body 20 is provided with first sliding grooves 22, the slider 10 is located on the upper portion of the main body 20, an end surface of the side of the slider 10 facing the main body 20 is provided with first bosses 11, and the first bosses 11 are embedded in the first sliding grooves 22. A front end of the main body 20 is provided with a cutting edge 21. The movable handle 30 is hinged to both the main body 20 and the slider 10, and the movable handle 30 may drive the slider 10 to move along the first sliding groove 22. A cheek portion of the main body 20 is provided with a trigger lock catch structure, the movable handle 30 may be pulled back and forth, and as shown in FIG. 6, an upper portion of the movable handle 30 is provided with a first feature portion 311 and a second feature portion 312 which are sequentially arranged from bottom to top, and the trigger lock catch structure abuts against the first feature portion 311 or the second feature portion 312. In this embodiment, it should be noted that the laminectomy rongeur takes a working direction as a front end; and the first feature portion 311 and the second feature portion 312 are not limited to a certain point feature only, but may also be a surface feature or a line feature.

When the trigger lock catch structure abuts against the first feature portion 311, the movable handle 30 may drive the slider 10 to move back and forth along the first sliding grooves 22, and in this case, the laminectomy rongeur is in a working state. It may be understood that when the laminectomy rongeur is working, the movable handle 30 may move relative to the main body 20 while being connected to the main body 20, that is, when a user holds the laminectomy rongeur by hand, pressing or releasing the movable handle 30 can move the slider 10 back and forth so as to achieve operation of punching and cutting soft tissue. When the movable handle 30 is pulled forwards, that is, the handle 30 needs to disengage from the normal working state, the trigger lock catch structure is converted from the first feature portion 311 to abutting against the second feature portion 312, the slider 10 leaves the first sliding grooves 22, the slider 10 forms a fixed angle with the main body 20 under a limiting action of the trigger lock catch structure, and in this case, the laminectomy rongeur is in a disassembled state.

Further, in this embodiment, the trigger lock catch structure is provided with a first sliding portion 41, a second sliding portion 42 and a trigger portion 40, which are sequentially arranged from left to right, and in actual production, in order to facilitate forming, assembly and disassembly, this part of the structure may be integrally formed, which improves stability of the whole member; when the laminectomy rongeur is in the working state, the first sliding portion 41 abuts against the first feature portion 311 of the movable handle 30; and when the laminectomy rongeur is in the disassembled state, the first sliding portion 41 abuts against the second feature portion 312 of the movable handle 30, and the trigger portion 40 is connected to a rear end of the slider 10 such that the slider 10 forms a fixed angle with the main body 20. More specifically, a rear end surface of the upper portion of the movable handle 30 protrudes to form an arc boss 31, and a lower surface of the arc boss 31 is in arc transition connection with a rear end surface of the movable handle 30 to form the first feature portion 311. An upper surface of the arc boss 31 is in arc transition connection with the rear end surface of the movable handle 30 to form the second feature portion 312; and the first sliding portion 41 can move on and abut against the first feature portion 311 or the second feature portion 312. When the overall structure is in a cleaning state, the trigger portion 40 is gently rotated such that a rear portion of the slider 10 is disposed below the trigger portion 40, and then the trigger portion 40 is released such that, under the action of the trigger portion 40, the slider 10 can be limited to the cleaning state so as to keep the rongeur open at a fixed angle in the cleaning state, and thus the rongeur will not be abnormally closed during cleaning and is easier to clean, disinfect and sterilize and more convenient to use.

Further, in this embodiment, the trigger lock catch structure comprises a trigger member 43, a trigger screw 70, and a torsion spring 60 sleeved on the trigger screw 70. The trigger member 43 is connected, in a clearance fit, to the main body 20 by means of the trigger screw 70, and the trigger member 43 can rotate around the trigger screw 70. The cheek portion of the main body 20 is provided with a hollow region in which the torsion spring 60 is arranged, and the trigger screw 70 penetrates from one side of the cheek portion of the main body 20 to the other opposite side of the cheek portion of the main body 20. Specifically, the trigger member 43 comprises the trigger portion 40. The trigger portion 40 is a key-shaped member, with an upper surface thereof being a flat surface, which is convenient for a user's thumb to come into contact with the flat surface of an upper surface of the trigger portion 40 and is more conducive to exerting force on the trigger portion 40, so that the structure can be operated with one hand during use, which is convenient. The end of the trigger portion 40 close to the movable handle 30 extends towards the movable handle 30 to form a third boss 44, an end surface of the third boss 44 in contact with the movable handle 30 forms the first sliding portion 41, and an arc-shaped surface, facing an interior of the third boss 44, provided at a lower portion of the third boss 44 forms the second sliding portion 42. The first sliding portion 41 abuts with the first feature portion 311 or the second feature portion 312, and the second sliding portion 42 abuts with the torsion spring 60. The trigger member 43 is connected to the main body 20 by means of the torsion spring 60, the trigger member 43 limits the movable handle 30, by means of torsion of the torsion spring 60. After the trigger member 43 is automatically restored, the movable handle 30 is limited again, such that the rongeur can achieve one-key restoration and has no need to assemble and disassemble for cleaning, there is no risk of losing parts, and the state can be switched with one key.

Specifically, when the laminectomy rongeur is in the working state, the first sliding portion 41 abuts against an upper edge of the first feature portion 311 of the movable handle 30. The user continues to press the handle, and the first sliding portion 41 slides at the first feature portion 311 of the movable handle 30 and finally abuts against the upper edge of the first feature portion 311 of the movable handle 30. Since the first bosses 11 arranged on the slider 10 are in the first sliding grooves 22 of the main body 20, when the handle is operated, the slider is driven to slide back and forth on the upper end of the main body 20. When the laminectomy rongeur needs to be switched from the working state to the disassembled state, the user releases the movable handle 30 and presses the trigger member 43, the first sliding portion 41 is disengaged from the first feature portion 311 and slides to the second feature portion 312, while the second sliding portion 42 abuts against an end of the torsion spring 60 and compresses the torsion spring 60. When the first bosses 11 at the rear of the slider 10 are disengaged from the first sliding grooves 22 at the rear of the main body 20, because the movable handle 30 is connected to the slider 10, the movable handle 30 drives the slider 10 to translate backwards while rotating clockwise, as the slider 10 continues to move backwards to the limit position, the sider rotates clockwise around the connection to the movable handle 30 until the sider forms a fixed angle with the main body 20. By means of rotating the trigger and then rotating the slider 10 to open at a certain angle, the rongeur can switch from the normal working state to the disassembled and cleaning state. The angle between the slider 10 and the main body 20 is restored, and then the movable handle 30 is rotated to make the torsion spring 60 rebound, and the manner of restoration of trigger can switch the rongeur from the disassembled and cleaning state to the normal working state.

Further, in this embodiment, a limiting pin 80 is further arranged in the hollow region on the cheek portion of the main body 20, the limiting pin 80 is in interference connection with an interior of a limiting hole of the main body 20, the limiting pin 80 is arranged below the first sliding portion 41, an axis of the limiting pin 80 is parallel to that of the trigger screw 70, one end of the torsion spring 60 abuts against the limiting pin 80 to make the torsion spring 60 in a stressed state, and the other end of the torsion spring abuts against the second sliding portion 42; and when the laminectomy rongeur is in the working state, the limiting pin 80 abuts against a lower portion of the first sliding portion 41, so as to make the first sliding portion 41 abut against the first feature portion 311.

Further, in this embodiment, the main body 20 is provided with a central screw 90, the movable handle 30 is hinged to the main body 20 by means of the central screw 90, the movable handle 30 may rotate around the central screw 90, the end of the movable handle 30 connected to the slider 10 is provided with a kidney-shaped hole 32, the slider 10 is connected to the movable handle 30 by means of a slider screw 50 in cooperation with the kidney-shaped hole 32, and the slider screw 50 may slide in the kidney-shaped hole 32; when the laminectomy rongeur is in the working state, the slider screw 50 is located in the middle of the kidney-shaped hole 32; and when the laminectomy rongeur is in the disassembled state, the slider screw 50 is located at an upper portion of the kidney-shaped hole 32.

Further, in this embodiment, a V-shaped leaf spring 100 is provided between the movable handle 30 and the main body 20. One end of the leaf spring 100 is connected to the movable handle 30, and the other end of the leaf spring is connected to the main body 20. Further, the movable handle 30 and the main body 20 are oppositely provided with a clamping portion, end portions of two ends of the leaf spring 100 are respectively provided with a fastener portion, and the fastener portions are detachably and fixedly connected to the clamping portion as a whole. Specifically, each clamping portion comprises two clamping pieces arranged parallel to each other, a clamping groove is formed between the two clamping pieces, the two clamping pieces are correspondingly provided with through holes, outer edges of the through holes and the clamping pieces are provided with notches, and the clamping portions are clamped into the through holes from the notches. Each fastener portion comprises symmetrical extending portions formed by an end portion of the leaf spring 100 extending towards the outside of the leaf spring 100, the two extending portions forming a T-shaped structure with the end portion of the leaf spring 100, and the extending portions being clamped in the through holes. The leaf spring 100 is provided with a fastener-type connection structure between same and the movable handle 30 and the main body 20 without the need of screws. The leaf spring 100 is a one-piece member, is different from a two-half leaf spring 100 of a traditional rongeur, may not be hinged or connected like a traditional two-half leaf spring 100, and is more convenient to clean, such that the position where the leaf spring 100 is connected to the movable handle 30 and the main body 20 is easier to clean, disinfect and sterilize, thereby avoiding bone residues and tissues residues and not easily causing cross infection.

Further, in this embodiment, a front portion and a rear portion of the upper portion of the main body 20 are respectively provided with first sliding grooves 22, a front portion and a rear portion of the slider 10 are respectively and correspondingly provided with first bosses 11, an end surface of the slider 10, facing the main body 20, between the two first bosses 11 is provided with a second sliding groove 12, the main body 20 between the two first sliding grooves 22 is correspondingly provided with a second boss 23, and the second boss 23 is embedded in the second sliding groove 12. By means of the cooperation between the first bosses 11 and the first sliding grooves 22, and between the second boss 23 and the second sliding groove 12, the slider 10 is better limited, such that the rongeur is not prone to being out of position when switched from the cleaning state to the normal state, and it is easier to switch the state. In addition, the end of the slider 10 close to the trigger lock catch structure is configured to be a smooth curved surface, with the curvature of the curved surface being of a minimum value at the highest point of the curved surface, thereby effectively reducing the height of the upper edge of the slider 10 to prevent the affection to the visual field during use due to excessive height.

When the detachable laminectomy rongeur of the embodiment of the present disclosure is in actual use:

when the first bosses 11 of the slider 10 slide in the first sliding grooves 22, with the limiting of the trigger lock catch structure to the movable handle 30, the slide block 10 may slide back and forth at the upper end of the main body 20 without being disengaged, and in this case, the rongeur being in the normal working state;

when the movable handle 30 rotates anticlockwise to a position, after the trigger member 43 may rotate clockwise by 50° around the trigger screw 70, the limiting of the trigger member 43 to the movable handle 30 is shifted to the rear, and under the elastic effect of the leaf spring 100, when the movable handle 30 is released, the movable handle 30 may rotate clockwise around the central screw 90 to the limit of the trigger member 43, the slider screw 50 slides to the top end of the kidney-shaped hole 32 of the movable handle 30, the slider 10 slides to the maximum limit at the upper end of the main body 20, and after the first bosses 11 at the front and rear ends of the slider 10 are disengaged from the corresponding first sliding grooves 22, the slider 10 may rotate around the slider screw 50, such that the slider 10 forms an angle with the upper end of the main body 20, and in this case, the rongeur is in the cleaning state; and after cleaning is completed, only the slider 10 needs to be rotated around the slider screw 50 and then attached to the upper end of the main body 20 again, the movable handle 30 is then rotated anticlockwise to a position, and under the torsion action of the torsion spring 60, the trigger member 43 is automatically restored to the normal working state to achieve the limiting action on the movable handle 30 when the movable handle is restored to the normal working state, and in this case, the rongeur is restored to the normal working state again from the cleaning state.

According to the structural design of the detachable laminectomy rongeur of the present disclosure, the gap between the main body 20 and the slider 10 can be thoroughly cleaned and disinfected so as to prevent remaining bone residues and soft tissue residues, thereby reducing the occurrence of cross infection and solving the problem of a laminectomy rongeur being difficult and time-consuming to clean and having easy-to-lose components, and the detachable laminectomy rongeur is simple to assemble and disassemble and is highly practical.

Obviously, the above embodiments of the present disclosure are merely examples for clear explanations of the present disclosure, instead of limiting the implementations of the present disclosure. For those of ordinary skill in the pertinent field, other different forms of variations or modifications may further be made on the basis of the illustration mentioned above. All embodiments are not necessary to be and cannot be exhaustively listed herein. Any modifications, equivalent substitutions, improvements, etc. made within the spirit and principles of the present disclosure shall fall within the scope of protection of the claims of the present disclosure.

What is claimed:

1. A detachable rongeur comprising:
a main body;
a slider; and
a movable handle,
an upper portion of the main body comprising first sliding grooves,
the slider being located on the upper portion and having a side facing the main body,
an end surface of the side facing the main body comprising first bosses that are embedded in the first sliding grooves,
a front end of the main body comprising a cutting edge,
the movable handle being hinged to the main body and the slider, the movable handle being capable of driving the slider to move along the first sliding grooves,
a cheek portion of the main body comprising a trigger lock catch structure,
the movable handle being capable of being pulled back and forth,
an upper portion of the movable handle comprising a first feature portion and a second feature portion that are sequentially arranged from bottom to top, and
the trigger lock catch structure being configured to directly abut against the first feature portion and the second feature portion in different operative states, such that:
when the trigger lock catch structure directly abuts against the first feature portion, the movable handle is configured to drive the slider to move back and forth along the first sliding grooves, and the detachable rongeur is in a working state, and
when the movable handle is pulled forwards, the trigger lock catch structure directly abuts against the second feature portion, the slider is disengaged from the first sliding grooves, the slider forms a fixed angle with the main body under a limiting action of the trigger lock catch structure, and the detachable rongeur is in a disassembled state;
wherein the trigger lock catch structure comprises a trigger member having first sliding portion and a trigger portion, and wherein:
when the detachable rongeur is in the working state, the first sliding portion directly abuts against the first feature portion of the movable handle, and
when the detachable rongeur is in the disassembled state, the first sliding portion directly abuts against the first feature portion of the movable handle, and the trigger portion is connected to a rear end of the slider such that the slider forms a fixed angle with the main body.

2. The detachable rongeur according to claim 1, wherein:
a rear end surface of the upper portion of the movable handle protrudes to form an arc boss, and a lower surface of the arc boss is in arc transition connection with a rear end surface of the movable handle to form the first feature portion;
an upper surface of the arc boss is in arc transition connection with the rear end surface of the movable handle to form the second feature portion; and
a first sliding portion is capable of moving on and directly abutting against the first feature portion or the second feature portion.

3. The detachable rongeur according to claim 1, wherein the detachable rongeur is configurable into a further disassembled state, in which the first sliding portion abuts against the second feature portion of the movable handle, and the trigger portion is not connected to a rear end of the slider such that the slider is not at a fixed angle with the main body.

4. The detachable rongeur according to claim 1, wherein:
the trigger lock catch structure comprises a trigger member, a trigger screw, and a torsion spring sleeved on the trigger screw,
the cheek portion of the main body comprises a hollow region in which the torsion spring is arranged, and
the trigger screw penetrates from one side of the cheek portion of the main body to an opposite side of the cheek portion of the main body.

5. The detachable rongeur according to claim 4, wherein:
the trigger member comprises the trigger portion, the trigger portion is a key-shaped member, with an upper surface of the trigger portion being a flat surface, an end of the trigger portion close to the movable handle extends towards the movable handle to form a third boss, an end surface of the third boss in contact with the movable handle forms the first sliding portion, an arc-shaped surface, facing an interior of the third boss, provided at a lower portion of the third boss forms the second sliding portion, the first sliding portion directly abuts with and comes into contact with the first feature portion or the second feature portion, and the second sliding portion abuts the torsion spring.

6. The detachable rongeur according to claim 4, wherein:

the hollow region of the cheek portion of the main body comprises a limiting pin arranged below the first sliding portion, the limiting pin has an axis parallel to an axis of the trigger screw, a first end of the torsion spring abuts against the limiting pin, and a second end of the torsion spring abuts against the second sliding portion, such that when the detachable rongeur is in the working state, the limiting pin abuts with a lower portion of the first sliding portion such that the first sliding portion abuts against the first feature portion.

7. The detachable rongeur according to claim 1, wherein:

the main body comprises a central screw, the movable handle is hinged to the main body by the central screw, and the movable handle is rotatable around the central screw.

8. The detachable rongeur according to claim 1, wherein:

an end of the movable handle connected to the slider comprises a kidney-shaped hole, and the slider is connected to the movable handle by a slider screw in cooperation with the kidney-shaped hole, such that:

when the detachable rongeur is in the working state, the slider screw is located in a middle of the kidney-shaped hole, and when the detachable rongeur is in the disassembled state, the slider screw is located in an upper portion of the kidney-shaped hole.

9. The detachable rongeur according to claim 1, further comprising a leaf spring between the movable handle and the main body, wherein a first end of the leaf spring is connected to the movable handle, and a second end of the leaf spring is connected to the main body, the leaf spring being an integrally formed structure.

10. The detachable rongeur according to claim 9, wherein the leaf spring is V-shaped.

11. The detachable rongeur according to claim 9, wherein the movable handle and the main body are oppositely provided with a clamping portion, the first end and the second end of the leaf spring each having an end portion comprising a fastener portion, the fastener portions being detachably and fixedly connected to the clamping portion as a whole.

12. The detachable rongeur according to claim 11, wherein:

the clamping portion comprises two clamping pieces parallel to each other, a clamping groove is formed between the two clamping pieces, the two clamping pieces are correspondingly provided with through holes, outer edges of the through holes and the clamping pieces comprise notches, and the clamping portion is clamped in the through holes from the notches.

13. The detachable rongeur according to claim 12, wherein:

each fastener portion comprises symmetrical extending portions formed by an end portion of the leaf spring extending towards an outside of the leaf spring, the two extending portions form a T-shaped structure with the end portion of the leaf spring, and the extending portions are clamped in the through holes.

14. The detachable rongeur according to claim 1, wherein:

a front portion and a rear portion of the upper portion of the main body are respectively provided with first sliding grooves, a front portion and a rear portion of the slider are respectively and correspondingly provided with first bosses, an end surface of the slider, facing the main body, between the first bosses comprises a second sliding groove, and the main body comprises a second boss embedded in the second sliding groove.

15. The detachable rongeur according to claim 1, wherein the main body and a holding portion of the movable handle are respectively provided with anti-slip lines.

16. The detachable rongeur according to claim 1, wherein an end of the slider close to the trigger lock catch structure is a smooth curved surface with a curvature being of a minimum value at a highest point of the curved surface.

17. The detachable rongeur according to claim 1, wherein the detachable rongeur is configured to be a laminectomy rongeur.

18. The detachable rongeur according to claim 1, wherein when the detachable rongeur is in the disassembled state, the trigger portion is abuts an outer surface of the rear end of the slider.

19. A detachable rongeur comprising:

a main body;

a slider; and a movable handle, an upper portion of the main body comprising first sliding grooves, the slider being located on the upper portion and having a side facing the main body, an end surface of the side facing the main body comprising first bosses that are embedded in the first sliding grooves, a front end of the main body comprising a cutting edge, the movable handle being hinged to the main body and the slider, the movable handle being capable of driving the slider to move along the first sliding grooves, a cheek portion of the main body comprising a trigger lock catch structure, the movable handle being capable of being pulled back and forth, an upper portion of the movable handle comprising a first feature portion and a second feature portion that are sequentially arranged from bottom to top, and the trigger lock catch structure being configured to abut against the first feature portion and the second feature portion in different operative states, such that:

when the trigger lock catch structure abuts against the first feature portion, the movable handle is configured to drive the slider to move back and forth along the first sliding grooves, and the detachable rongeur is in a working state, and when the movable handle is pulled forwards, the trigger lock catch structure abuts against the second feature portion, the slider is disengaged from the first sliding grooves, the slider forms a fixed angle with the main body under a limiting action of the trigger lock catch structure, and the detachable rongeur is in a disassembled state;

wherein the detachable rongeur further comprises:

a leaf spring between the movable handle and the main body, wherein a first end of the leaf spring is connected to the movable handle, and a second end of the leaf spring is connected to the main body, the leaf spring being an integrally formed structure, wherein the movable handle and the main body are oppositely provided with a clamping portion, the first end and the second end of the leaf spring each having an end portion comprising a fastener portion, the fastener portions being detachably and fixedly connected to the clamping portion as a whole, and wherein:

the clamping portion comprises two clamping pieces parallel to each other, a clamping groove is formed between the two clamping pieces, the two clamping pieces are correspondingly provided with through holes, outer edges of the through holes and the clamping pieces comprise notches, and the clamping portion is clamped in the through holes from the notches.

* * * * *